United States Patent
Sun et al.

(10) Patent No.: US 7,175,433 B2
(45) Date of Patent: *Feb. 13, 2007

(54) DENTAL MATERIAL AND METHOD

(75) Inventors: Benjamin Sun, York, PA (US);
Andrew M Lichkus, York, PA (US)

(73) Assignee: Dentsply International Inc., York, PA (US)

(*) Notice: Subject to any disclaimer, the term of this patent is extended or adjusted under 35 U.S.C. 154(b) by 156 days.

This patent is subject to a terminal disclaimer.

(21) Appl. No.: 10/249,344

(22) Filed: Apr. 2, 2003

(65) Prior Publication Data

US 2003/0153645 A1    Aug. 14, 2003

Related U.S. Application Data

(63) Continuation-in-part of application No. 10/306,096, filed on Nov. 27, 2002, now Pat. No. 6,799,969, which is a continuation-in-part of application No. 10/106,741, filed on Mar. 26, 2002, now abandoned, which is a continuation-in-part of application No. 09/682,440, filed on Sep. 4, 2001, now Pat. No. 6,592,369, which is a continuation of application No. 09/670,364, filed on Sep. 26, 2000, now abandoned.

(60) Provisional application No. 60/237,523, filed on Oct. 4, 2000, provisional application No. 60/201,705, filed on May 3, 2000, provisional application No. 60/164,893, filed on Nov. 10, 1999.

(51) Int. Cl.
*A61C 13/00* (2006.01)
(52) U.S. Cl. .................. 433/167; 433/199.1; 523/115
(58) Field of Classification Search ............... 433/167, 433/199.1; 523/109, 113, 115, 116; 264/16, 264/17, 18, 119
See application file for complete search history.

(56) References Cited

U.S. PATENT DOCUMENTS

| | | | |
|---|---|---|---|
| 4,017,971 A | 4/1977 | Hazar | 32/2 |
| 4,094,067 A | 6/1978 | Hazar | 32/2 |
| 4,097,992 A | 7/1978 | Hazar | 32/2 |
| 4,133,110 A | 1/1979 | Bernstein et al. | 32/2 |
| 4,161,065 A | 7/1979 | Gigante | 32/2 |
| 4,175,322 A | 11/1979 | Tureaud | 433/171 |
| 4,247,287 A | 1/1981 | Gigante | 433/199 |
| 4,248,807 A | 2/1981 | Gigante | 264/18 |
| 4,259,074 A | 3/1981 | Link | 433/214 |
| 4,345,900 A | 8/1982 | Katz et al. | 433/171 |
| 4,375,966 A | 3/1983 | Freeman | 433/37 |
| 4,457,818 A | 7/1984 | Denyer et al. | 204/159 |
| 4,468,222 A | 8/1984 | Cohen | 433/199 |
| 4,543,063 A | 9/1985 | Cohen | 433/175 |
| 4,551,098 A | 11/1985 | Blair | 433/171 |
| 4,609,351 A | 9/1986 | Blair | 433/55 |
| 4,705,476 A | 11/1987 | Blair | 433/171 |
| 4,721,735 A | 1/1988 | Bennett et al. | 522/71 |
| 4,813,875 A | 3/1989 | Hare | 433/214 |
| 4,978,298 A | 12/1990 | Eliasz | 433/213 |
| 5,063,255 A | 11/1991 | Hasegawa et al. | 522/96 |
| 5,177,120 A | 1/1993 | Hare et al. | 433/37 |
| 5,213,498 A | 5/1993 | Pelerin | 433/37 |
| 5,304,063 A | 4/1994 | Ginsburg | 433/199 |
| 5,403,186 A | 4/1995 | Ginsburg | 433/199 |
| 5,591,786 A | 1/1997 | Oxman et al. | 533/109 |
| 5,635,545 A | 6/1997 | Oxman et al. | 523/115 |
| 5,711,668 A | 1/1998 | Huestis | 433/167 |
| 5,993,208 A | 11/1999 | Jonjic | 433/50 |
| 6,031,015 A | 2/2000 | Ritter et al. | 522/77 |
| 6,057,383 A | 5/2000 | Volkel et al. | 523/116 |
| 6,244,864 B1 | 6/2001 | Fujiwara et al. | 433/71 |
| 6,387,981 B1 | 5/2002 | Zhang et al. | 523/117 |
| 2004/0077742 A1* | 4/2004 | Hilger et al. | 522/1 |

FOREIGN PATENT DOCUMENTS

| | | |
|---|---|---|
| EP | 0 630 640 | 12/1994 |
| EP | 813 856 | 12/1997 |
| EP | 1 042 994 | 10/2000 |
| GB | 2 225 333 | 5/1990 |

OTHER PUBLICATIONS

Moszner N. et al; "Synthesis Characterization and Polymerization of Waxy Monomers", 1997.

* cited by examiner

*Primary Examiner*—Todd E. Manahan
(74) *Attorney, Agent, or Firm*—Daniel W. Sullivan; James B. Bieber; Douglas J. Hura

(57) ABSTRACT

The invention provides a dental composition including filler and a polymerizable dental material selected from the group consisting of wax-like polymerizable dental material and restorative paste wax polymerizable dental material. The dental composition is useful as restorative material and for making artificial teeth, crowns and bridges of high strength dental polymeric material.

3 Claims, No Drawings

DENTAL MATERIAL AND METHOD

CROSS REFERENCE TO RELATED APPLICATIONS

This application is a continuation-in-part of U.S. patent application Ser. No. 10/106,741 filed Mar. 26, 2002 now abandoned which is a continuation-in-part of U.S. patent application Ser. No. 09/682,440 filed Sep. 4, 2001 now U.S. Pat. No. 6,592,369 which is a continuation-in-part of U.S. patent application Ser. No. 09/670,364 filed Sep. 26, 2000, (abandoned). This application is a continuation-in-part of U.S. patent application Ser. No. 10/306,096 filed Nov. 27, 2002 now U.S. Pat. No. 6,799,969 which is a continuation of U.S. patent application Ser. No. 09/670,364 filed Sep. 26, 2000, (abandoned). The benefit is claimed of U.S. provisional patent application Ser. No. 60/237,523 filed Oct. 4, 2000, U.S. Provisional Patent Application Ser. No. 60/201,705 filed May 3, 2000, and U.S. Provisional Patent Application Ser. No. 60/164,893 filed Nov. 10, 1999.

DETAILED DESCRIPTION

The invention provides wax-like polymerizable dental material and restorative paste wax polymerizable dental material. Wax-like material is flowable at and above 40° C., and becomes dimensionally stable at and below 23° C., within 5 minutes. Restorative paste wax material is flowable at and above 50° C., and becomes dimensionally stable at and below 37° C., within 5 minutes. These polymerizable dental material may include filler particles, fiber and/or rubber-modified high molecular weight resin. These polymerizable dental materials are useful in tooth restorative fillings, adhesives, cements, denture base materials, orthodontic materials and sealants, for repair of defects in natural dentition, and to form crowns, bridges, full dentures, partial dentures, denture liners, custom trays, artificial teeth, repairs for natural teeth, veneers, denture repairs, denture reline, night guards, splints, retainers, orthodontic components, provisional dental devices, inlays, onlays, orthodontic appliances, oral orthopedic appliances, temporary dentures, temporary partial dentures, maxillofacial prostheses, obturators, and occular prostheses.

Polymerizable dental material in accordance with the invention may include from 0 to about 95 percent by weight filler particles. In a preferred embodiment of the invention polymerizable dental materials include from about 5 to about 90 percent by weight filler. More preferably, these polymerizable dental materials include from about 20 to about 85 percent by weight filler. Most preferably, these polymerizable dental materials include from about 40 to about 80 percent by weight filler.

The filler particles have a range of particles sizes from 0.01 micrometers to 10 micrometers. The filler particles preferably include organic and/or inorganic particles, and preferably reduce polymerization shrinkage, improve wear resistance and modify the mechanical and physical properties. Preferred fillers are glasses formed from or including, barium, calcium, strontium, lanthanum, tantalum, and/or tungsten silicates and aluminates and/or aluminosilicates, silica, quartz, ceramics, nanoparticles. Peferably the filler particles have a range of particle sizes of from 0.01 micrometers to 10 micrometers.

The polymerizable dental materials of the invention are quickly and easily reshaped, for example by warming, and shaping it while warm and then allowing it to cool to body (37° C.) or room temperature (23° C.). The cooled polymerizable dental materials may be worked for example by packing, molding, shaping, and/or carving. The worked polymerizable dental materials are cured.

The polymerizable dental materials of the invention preferably include from about 1 to about 100 percent by weight of a crystalline resin and from about 0 to 99 percent by weight of an amorphous component. When heated, the polymerizable dental materials soften and are more flowable and less crystalline.

Wax-like polymerizable dental material and restorative paste wax polymerizable dental material of the invention may include pigments, initiators, catalysts, stabilizers, plasticizers and fibers. Preferred stabilizers are butylated hydroxytoluene (BHT) and the methyl ether of hydroquinone (MEHQ).

Polymerizable dental materials of the invention may include one or more initiating systems to cause them to harden promptly. Light curable wax-like polymerizable dental composites preferably include a light sensitizer, for example camphorquinone, 2,4,6- trimethylbenzoyidiphenylphosphine oxide, or methyl benzoin which causes polymerization to be initiated upon exposure to activating wavelengths of light; and/or a reducing compound, for example tertiary amine.

A room temperature or heat activating catalyst system is preferably included in polymerizable dental materials of the invention. For example a peroxide capable of producing free radicals when activated by a reducing agent at room temperature or by heating. Preferred peroxides include benzyl peroxide and lauroyl peroxide.

Polymerizable dental materials of the invention are preferably rapidly partially recrystallizable. Rapid recrystallizability provides the densification of the polymeric products and a combination of flowability and dimensional stability, depending on its temperature prior to polymerization. When polymerized, the crystallized phase melts effective resulting in volume expansion, which offsets polymerization shrinkage. Thus, the polymeric products are low shrinkage and low stress restoration. "Crystallinity" as used herein refers to regularity and order within a material resulting in a heat of fusion of at least 1.0 J/g at and below 50° C. Heat of Fusion as used herein refers to enthalpy of fusion as determined by ASTM 793-95. Percent crystallinity is determined by measuring the heat of fusion using differential scanning calorimetry according to ASTM test method E 793-95.

A preferred embodiment of the invention provides a high strength dental polymeric material formed by light curing wax-like polymerizable dental material and restorative paste wax polymerizable dental material. Preferably the high strength dental polymeric material has a flexural modulus of at least 500,000 psi and a flexural strength of at least 7,000 psi. More preferably, high strength dental polymeric material has a flexural modulus of at least 800,000 psi and a flexural strength of at least 10,000 psi. Most preferably, high strength dental polymeric material has a flexural modulus of at least 1,200,000 psi and a flexural strength of at least 15,000 psi. "Flexural strength, and flexural modulus" as used herein refers to results of testing according to ASTM D790 (1997).

"Wax-like" as used herein refers to material which is flowable (fluid) at and above 40° C., and becomes dimensionally stable (solidifies: i.e. is nonfluid) at least at and below 23° C., within 5 minutes. Thus, wax-like material is flowable when it is at and above 40° C., and becomes dimensionally stable when it is at and below 23° C. Flowable wax-like material having a temperature from 100° C. to 40° C., becomes dimensionally stable within 5 minutes by cooling by exposure to an ambient temperature between 37° C. and 0° C. Flowable wax-like composite paste having a temperature from 100° C. to 40° C., becomes dimensionally stable within (in order of increasing preference) 4, 2, 1 or 0.5 minutes by cooling by exposure to an ambient temperature between 23° C. and 0° C.

"Restorative Paste Wax" as used herein refers to material which is flowable (fluid) at and above 50° C., and becomes dimensionally stable (solidifies: i.e. is nonfluid) at least at and below 37° C., within 5 minutes. Thus, restorative paste wax is flowable when it is at and above 50° C., and becomes dimensionally stable when it is at and below 37° C. Flowable restorative paste wax having a temperature from 100° C. to 50° C., becomes dimensionally stable within 5 minutes by cooling by exposure to an ambient temperature between 37° C. and 0° C. Flowable restorative paste wax having a temperature from 100° C. to 50° C., becomes dimensionally stable within (in order of increasing preference) 4, 2, 1 or 0.5 minutes by cooling by exposure to an ambient temperature between 37° C. and 0° C. Restorative paste wax may be flowable throughout all of the temperature range from 49° C. to 38° C.; it may be dimensionally stable throughout all of the temperature range from 49° C. to 38° C.; or it may be flowable in part and dimensionally stable in part of the temperature range from 49° C. to 38° C. Dimensional stability is determined by testing according to ADA (American Dental Association) consistency test specification 19, paragraph 4.3.4, JAVA Vol. 94, April, 1977, pages 734–737 at 23° C. Fluids change shape uniformly in response to external force imposed on them (see Hawley's Condensed Chemical Dictionary 1997, page 507, at fluid.

In order of increasing preference polymerization shrinkage of wax-like polymerizable dental material and restorative paste wax polymerizable dental material of the invention is less than 3 percent by volume, less than 2 percent by volume, less than 1.5 percent by volume, less than 1 percent by volume. In order of increasing preference polymerization shrinkage of restorative paste wax polymerizable dental material of the invention is less than 3 percent by volume, less than 2 percent by volume, less than 1.5 percent by volume, less than 1 percent by volume.

"High strength dental polymeric material" as used herein refers to material having a polymeric matrix having a flexural modulus of at least 250,000 psi and a flexural strength of at least 5,000 psi. Preferably high strength dental polymeric material has a polymeric matrix having a flexural modulus of at least 300,000 psi and a flexural strength of at least 7,000 psi, and an un-notched impact strength of at least 2 foot-pounds/inch. More preferably high strength dental polymeric material in order of increasing preference has a polymeric matrix having a flexural modulus of at least 350,000 psi and a flexural strength of at least 12,000 psi, and an un-notched impact strength of at least 3.0 foot-pounds/inch. High strength dental polymeric material is preferably formed into dental products including full dentures, partial dentures, denture relines, night guards, crowns and bridges by polymerization of wax-like polymerizable dental material or restorative paste wax polymerizable dental material.

A preferred embodiment of the invention provides a prepared cavity in a tooth in a patient's mouth, which is then filled by injection from a syringe of dental filling material in accordance with the invention. Preferably the syringe is heated to from 42° C. to 60° C., and has a readily disconnected and interchangeable nozzle with a generally cylindrical internal passage having an internal diameter of from about 0.5 mm to about 5.0 mm. The dental filling material cools and solidifies rapidly in the prepared cavity in the tooth to about 37° C. Thus, a syringe is provided having an inner chamber and a nozzle. The nozzle has a nozzle passage in fluid flow communication with the inner chamber. The inner chamber encloses wax-like polymerizable dental material or restorative paste wax polymerizable dental material. Then the polymerizable dental material is polymerized to form a high strength dental polymeric material.

A preferred embodiment of the invention provides a prepared cavity in a tooth in a patient's mouth, which is then filled by positioning in the prepared cavity a composition including at least 40 percent by weight filler and a polymerizable dental material selected from the group consisting of wax-like polymerizable dental material and restorative paste wax polymerizable dental material. Then the polymerizable dental material is light cured to form high strength dental polymeric material with a shrinkage during polymerization of less than 2 percent by volume. The polymerizable dental material includes a portion of crystals, which melt during polymerization. The crystals are believed to be crystals of oligomer and/or crystals of monomer. The volume of the liquid formed by melting the crystals is greater than the volume of the crystals. This expansion reduces the shrinkage of the polymerizable dental material caused by polymerization.

In the following examples, unless otherwise indicated, all parts and percentages are by weight; Lucirin TPO refers to 2,4,6- trimethylbenzoyldiphenylphosphine oxide made by BASF.

EXAMPLE 1

Preparation of Oligomer A reactor was charged with 1176 grams of trimethyl-1,6-diisocyanatohexane (5.59 mol) and 1064 grams of bisphenol A propoxylate (3.09 mol) under dry nitrogen flow and heated to about 65° C. under positive nitrogen pressure. To this reaction mixture, 10 drops of catalyst dibutyltin dilaurate were added. The temperature of the reaction mixture was maintained between 65° C. and 140° F. for about 70 minutes and followed by additional 10 drops of catalyst dibutyltin dilaurate. A viscous paste-like isocyanate end-capped intermediate product was formed and stirred for 100 minutes. To this intermediate product, 662 grams (5.09 mol) of 2-hydroxyethyl methacrylate and 7.0 grams of BHT as an inhibitor were added over a period of 70 minutes while the reaction temperature was maintained between 68° C. and 90° C. After about five hours stirring under 70° C., the heat was turned off, and oligomer was collected from the reactor as semi-translucent flexible solid and stored in a dry atmosphere.

EXAMPLE 2

Preparation of Oligomer A reactor was charged with 150 grams of 1,6-diisocyanatohexane and 200 grams of bisphenol A propoxylate under dry nitrogen flow and heated to about 56° C. under positive nitrogen pressure. To this reaction mixture, 0.12 gram of catalyst dibutyltin dilaurate was added. The temperature of the reaction mixture was maintained between 65° C. and 80° C. for about 3.5 hours. To this isocyanate end-capped intermediate product, 82.96 grams of 2-hydroxyethyl methacrylate and 2.15 grams of BHT as an inhibitor were added over a period of 50 minutes while the reaction temperature was maintained between 55° C. and 75° C. After about five hours stirring, the heat was turned off, and oligomer was collected from the reactor as semi-translucent flexible solid and stored in a dry atmosphere.

EXAMPLE 3

Preparation of Monomer A reaction flask was charged with 700 grams of 1,6-diisocyanatohexane and heated to about 70° C. under a positive nitrogen pressure. To this reactor were added 1027 grams of 2-hydroxyethyl methacrylate, 0.75 gram of catalyst dibutyltin dilaurate and 4.5 grams of butylated hydroxy toluene (BHT). The addition was slow and under dry nitrogen flow over a period of two hours. The temperature of the reaction mixture was maintained between 70° C. and 90° C. for another two hours and followed by the addition of 8.5 grams of purified water. One hour later, the reaction product was discharged as clear liquid into plastic containers and cooled to form a white solid and stored in a dry atmosphere.

EXAMPLE 4

Preparation of Monomer A reaction flask was charged with 168 grams of 1,6-diisocyanatohexane and heated to about 70° C. under a positive nitrogen pressure. To this reactor were added 228 grams of 2-hydroxyethyl acrylate, 0.12 gram of catalyst dibutyltin dilaurate and 0.86 grams of butylated hydroxy toluene (BHT). The addition was slow and under dry nitrogen flow over a period of two hours. The temperature of the reaction mixture was maintained between 70° C. and 85° C. for another three hours and followed by the addition of 0.9 grams of purified water. One hour later, the reaction product was discharged as clear liquid into plastic containers and cooled to form a white solid and stored in a dry atmosphere.

EXAMPLE 5

Preparation of Monomer A reaction flask was charged with 151.25 grams of octadecyl isocyanate and heated to about 70° C. under a positive nitrogen pressure. To this reactor were added 125.3 grams of caprolactone 2-(methacryloyloxy)ethyl ester, 0.12 gram of catalyst dibutyltin dilaurate and 0.58 grams of butylated hydroxy toluene (BHT). The addition was slow and under dry nitrogen flow over a period of two hours. The temperature of the reaction mixture was maintained between 70° C. and 85° C. for another 2.5 hours, the reaction product was discharged as clear liquid into plastic containers and cooled to form a semi-opaque solid and stored in a dry atmosphere.

EXAMPLE 6

Preparation of Monomer A reaction flask was charged with 200 grams of octadecyl isocyanate and heated to about 78° C. under a positive nitrogen pressure. To this reactor were added 90.6 grams of 2-hydroxyethyl methacrylate, 0.14 gram of catalyst dibutyltin dilaurate and 0.58 grams of butylated hydroxy toluene (BHT). The addition was slow and under dry nitrogen flow over a period of two hours. The temperature of the reaction mixture was maintained between 70° C. and 85° C. for another 3 hours, the reaction product was discharged as clear liquid into plastic containers and cooled to form a white solid and stored in a dry atmosphere.

EXAMPLES 7A THROUGH 7D

Tables 1 and 2 show the components of the compositions of Examples 7A through 7D. The compositions of Examples 7A through 7D were prepared by mixing the components shown in Tables 1 and 2 at 90° C.

TABLE 1

| COMPONENTS | Example 7A (grams) | Example 7B (grams) |
|---|---|---|
| Oligomer of Example 2 | 14.9 | 29.5 |
| Cyclohexane dimethanol diacrylate | 9.9 | 19.7 |
| Camphorquinone | 0.14 | 0.21 |
| N,N-dimethyl-aminoneopentyl acrylate | 0.46 | 0.74 |
| Methacrylic Acid | 0.23 | 0.37 |
| Butylated Hydroxytoluene | 0.01 | 0.02 |
| γ methacryloxypropylsilane | 0.16 | 0.26 |
| silanated barium aluminoflurosilicate glass (BAFG)* | 28 | 18.6 |
| silanated barium aluminoflurosilicate glass (BAFG)** | 40.3 | 26.7 |
| silanated fumed silica*** ($SiO_2$) | 5.9 | 3.9 |

*particles having an average particle size of from about 1 to about 10 micrometers.
**particles having an average particle size of from about 0.1 to about 1 micrometers.
***particles having an average particles size of from about 0.01 to about 0.04 micrometers.

TABLE 2

| COMPONENTS | Example 7C (grams) | Example 7D (grams) |
|---|---|---|
| Titanium dioxide | 0.065 | |
| Iron oxide | 0.0086 | 0.0007 |
| Red-Brown Pigment | 0.0011 | 0.0003 |
| Black Pigment | 0.0011 | |
| Ultramarine Blue Pigment | | 0.0009 |
| a blend of 82.99% ZnO, 16.18% Magnesium carbonate, 0.62% Lithium sulfate and 0.21% Sulfur, (sublimed powder). [115 Phosphor] | 0.032 | 0.012 |
| dihydroxy terepthalate acid ester [FLU-L-BLU] | 0.011 | 0.0061 |
| Monomer of Example 4 | 1.36 | 1.4 |
| Monomer of Example 5 | | 2 |
| Octadecyl acrylate | 1.13 | 1.4 |
| Monomer of Example 3 | 5.42 | 5.3 |
| Oligomer of Example 1 | 12.2 | 12.6 |
| Monomer of Example 6 | 2.26 | |
| 2,4,6-trimethylbenzoyl-diphenylphosphine oxide (Lucirin TPO) | 0.08 | 0.05 |
| Camphorquinone | 0.019 | 0.044 |
| N,N-dimethyl-aminoneopentyl acrylate | 0.064 | 0.152 |
| Methacrylic Acid | 0.032 | 0.076 |
| Butylated Hydroxytoluene | 0.002 | 0.004 |
| γ methacryloxypropylsilane | 0.023 | 0.054 |
| silanated fumed silica*** ($SiO_2$) | 15.46 | 15.4 |
| silanated barium aluminoflurosilicate glass (BAFG)** | 46.38 | 46.3 |
| silanated barium aluminoflurosilicate glass (BAFG)* | 15.46 | 15.6 |

*particles having an average particle size of from about 1 to about 10 micrometers.
**particles having an average particle size of from about 0.1 to about 1 micrometers.
***particles having an average particles size of from about 0.01 to about 0.04 micrometers.

Table 3 shows the physical properties of the products of Examples 7A 7D, which have been polymerized by light curing.

TABLE 3

| Property | Example 7A | Example 7B | Example 7C | Example 7D |
| --- | --- | --- | --- | --- |
| Localized Wear - mm$^3$ (samples were cured for 10 minutes in the Eclipse light curing unit (voltage at 37.5 V, blowers at 80%) | 0.009 | 0.013 | 0.021 | |
| Localized Wear - mm$^3$ (samples were cured by handheld curing light for 90 seconds) | | | 0.049 | 0.084 |
| Flexural Strength psi | | | 18,080 | 17,160 |
| Flexural Modulus kpsi | | | 1,645 | 1550 |
| Compressive Strength - MPa | | | 223 | 298 |
| Water Sorption - μg/mm$^3$ | | | 14.0 | 13.4 |

Compressive Strength of the polymerized composite compositions of Examples 7A through 7D was measured using 50 kN load cell set to run at 2,000 pounds with crosshead speed at 2 inches (50.8 mm)/per minute. Compressive strength testing specimens were prepared by following the procedure of U.S. Pat. No. 6,387,981. Each composite was packed into a 4 mm inside diameter glass tube, capped with silicone rubber plugs and axially compressed at about 0.28 MPa for 15 minutes, then light cured for 10 minutes in Eclipse light curing unit (voltage at 37.5 V, blowers at 80 percent). Cured samples were cut on a diamond saw to form cylindrical plugs 8 mm long and stored in distilled water at 37° C. for 24 hours and then measured for compressive strength.

Flexural Strength and Flexural Modulus of the polymerized composite compositions of Examples 7C and 7D were measured by using three-point bend test on Instron bending unit according to ASTM 790 (7997). Samples were cured in metal molds in an Eclipse light curing unit for 10 minutes (voltage at 37.5 V, blowers at 80% from 5.5–10 minutes).

EXAMPLE 8

Filling Material A cavity in an natural tooth in a patient's mouth is prepared by drilling, and then brushing onto the drilled cavity about 0.02 ml of PRIME & BOND NT dual cure bonding agent, sold by Dentsply International Inc. Then the bonding agent is light cured by impinging light thereon for 30 seconds from a Spectrum 800 light curing unit sold by Dentsply International Inc. The prepared cavity is then filled with 0.2 g of the product of Example 7A, which is then light cured by impinging light thereon for 30 seconds from a Spectrum 800 light curing unit sold by Dentsply International Inc.

EXAMPLE 9A

Crown A crown is formed by molding about 0.5 g of the product of Example 7B. A surface of natural tooth in a patient's mouth is prepared for the crown by cutting and polishing, and then brushing onto the polished surface about 0.05 ml of PRIME & BOND NT dual cure bonding agent, sold by Dentsply International Inc. Then the crown is set onto the prepared surface. The crown and the bonding agent are then light cured by impinging light thereon for 60 seconds from a Spectrum 800 light curing unit sold by Dentsply International Inc.

EXAMPLE 9B

Veneer A veneer is formed by molding about 0.3 g of the product of Example 7C. A surface of natural tooth in a patient's mouth is prepared for the veneer by cutting and polishing, and then brushing onto the polished surface 0.03 ml of PRIME & BOND NT dual cure bonding agent, sold by Dentsply International Inc. Then the veneer is set onto the prepared surface. The veneer and the bonding agent are then light cured by impinging light thereon for 60 seconds from a Spectrum 800 light curing unit sold by Dentsply International Inc.

EXAMPLE 9C

Filling Material A natural dentition in a patient's mouth in need of restoration is selected. A cavity in the tooth is prepared by drilling, and then brushing onto the drilled cavity 0.02 ml of PRIME & BOND NT dual cure bonding agent, sold by Dentsply International Inc. Then the bonding agent is light cured by impinging light thereon for 30 seconds from a Spectrum 800 light curing unit sold by Dentsply International Inc. The prepared cavity is then filled by injection into the cavity of 0.2 g of the product of Example 7D from a syringe having a nozzle with an internal passage diameter of about 2 mm. The syringe is warmed to 50° C., and has a chamber filled with the dental filling material product of Example 7D. The dental filling material cools to 37° C. and solidifies rapidly with excellent shape stability. The cooled filling material is carved and sculptured to conform to the contour and shape of the tooth. The cooled dental filling material is then light cured by impinging light thereon for 30 seconds from a Spectrum 800 light curing unit sold by Dentsply International Inc.

EXAMPLE 10

Green Tooth A tooth is formed by molding 0.6 g of the product of Example 7C into the shape of a natural tooth.

EXAMPLE 11

High Strength Tooth The tooth formed in Example 10 is light cured by impinging light thereon for 10 minutes from an Eclipse light curing unit sold by Dentsply International Inc. A high strength polymeric artificial tooth is formed which has a polymerization shrinkage of less than 2 percent by volume.

It should be understood that while the present invention has been described in considerable detail with respect to certain specific embodiments thereof, it should not be considered limited to such embodiments but may be used in other ways without departure from the spirit of the invention and the scope of the appended claims.

The invention claimed is:
1. A high strength dental composition comprising filler and a polymerizable dental material selected from the group consisting of wax-life polymerizable dental material and restorative paste wax polymerizable dental material.
2. The composition of claim 1, wherein said filler comprises nanoparticles.
3. The composition of claim 1 wherein said polymerizable dental material is shaped and polymerized to form polymeric material having a flexural modulus of at least 400,000 psi and a flexural strength of at least 7,000 psi.

* * * * *